(12) United States Patent
Taylor et al.

(10) Patent No.: US 8,426,218 B2
(45) Date of Patent: Apr. 23, 2013

(54) FIXATION FILTER ASSEMBLY

(75) Inventors: Craig D. Taylor, Mashpee, MA (US);
Kenneth W. Doherty, Falmouth, MA (US); Susumu Honjo, Falmouth, MA (US)

(73) Assignee: McLane Research Laboratories, Inc., East Falmouth, MA (US)

( * ) Notice: Subject to any disclaimer, the term of this patent is extended or adjusted under 35 U.S.C. 154(b) by 373 days.

(21) Appl. No.: 12/907,330

(22) Filed: Oct. 19, 2010

(65) Prior Publication Data

US 2012/0091067 A1    Apr. 19, 2012

(51) Int. Cl.
*G01N 1/28*    (2006.01)

(52) U.S. Cl.
USPC ......... 436/177; 436/174; 436/176; 435/307.1

(58) Field of Classification Search .................. 210/749, 210/764, 765; 436/174, 177, 176, 63; 435/307.1
See application file for complete search history.

(56) References Cited

U.S. PATENT DOCUMENTS

| | | |
|---|---|---|
| 4,086,161 A | 4/1978 | Burton |
| 4,302,333 A | 11/1981 | Cosack et al. |
| 4,368,691 A | 1/1983 | Brune |
| 4,637,719 A | 1/1987 | Herman |
| 5,977,153 A | 11/1999 | Camiener |
| 6,123,859 A | 9/2000 | Lee et al. |
| 2002/0164677 A1 | 11/2002 | Giovannoni et al. |
| 2003/0131800 A1 | 7/2003 | Yoshimura et al. |
| 2003/0196947 A1 | 10/2003 | Gundrum et al. |
| 2005/0167351 A1 | 8/2005 | Herman et al. |
| 2008/0053919 A1 | 3/2008 | Martin et al. |
| 2008/0099407 A1* | 5/2008 | Eilers et al. ................... 210/749 |

OTHER PUBLICATIONS

International Search Report and Written Opinion of the International Searching Authority issued in related PCT/US11/56750 (10 pgs) with date of mailing Feb. 29, 2012.

* cited by examiner

*Primary Examiner* — Yelena G Gakh
*Assistant Examiner* — Christopher A Hixson
(74) *Attorney, Agent, or Firm* — Grossman, Tucker, Perreault & Pfleger, PLLC (57) ABSTRACT

A filter assembly is provided for collecting samples in a fluid environment, the assembly utilizing a laminar convective flow to cause the flow of a preservative/fixative and a filtrate through a filter. A substantially concave dead space around the filter is flushed free of the preservative and the differential in density of the preservative and filtrate causes the more dense fluid to collect in the reservoir and preserve the collected specimen.

12 Claims, 6 Drawing Sheets

SAMPLING
CONFIGURATION

FIXATION FILTER ASSEMBLY

FIELD

The present disclosure relates to sample collection and handling in a fluid environment, more particularly to the collection and fixation of microorganisms and particulate samples in aquatic ecosystems. More generally, the present disclosure relates to sampling in any water environment, such as in reservoirs and/or any natural or man-made water containment configuration as well as with any industry that may be concerned with water quality.

BACKGROUND

Sample collection and handling in a fluid environment is of course the subject of a variety of reports. Marine research typically requires continuous information on the marine food chain which may generally consist of (1) aquatic bacteria and protists, (2) phytoplankton (3) zooplankton and (4) fish as well as higher forms, crustaceans, reptiles, marine mammals, etc., where each may become a food source for the next in ascending order. Bacteria, protists, phytoplankton and zooplankton may be measured in oceans and studied for their dependence and effect on fisheries and environmental health. Information may be required on their abundance and vertical and horizontal distributions in continental shelf waters, deep oceans and inland waters. Acquiring the data accurately, continuously and with wide spatial coverage remains an on-going problem.

It can be noted that the U.S. Coast Guard, for purposes of operationally defining relevant classes of organisms (from the perspective of invasive species in shipping ballast water) is as follows: zooplankton—organisms that are ≧50 μm in minimum dimension; phytoplankton/protozoa—organism that are <50 μm and ≧10 μm; bacteria—organisms <10 μm in minimum dimension (this operational group will also include many of the smaller phototrophic phytoplankton and blue-green bacteria).

Accordingly, a need exists for a method and apparatus that may automate the collection of samples for critical assays, including enumeration, phylogenetic identity, molecular and metabolic functioning and viability of the various microbial, phytoplankton and zooplankton components of the food chain. More particularly, the method may comprise automated in situ rate studies involving tracer incubations and sample preservation.

SUMMARY

In a first exemplary embodiment, the present disclosure relates to a filter assembly for flow of filtrate comprising an inlet and outlet for flow of first fluid filtrate having a density $D_1$ and a reservoir to contain a second fluid having a density $D_2$, an interior space for filter media and a reservoir plate to partition the reservoir from the interior space wherein the reservoir plate includes at least two openings in communication with the reservoir and the interior space. The second fluid in the reservoir is therefore capable of exchange with the first fluid in the interior space due to a differential density of the first and second fluids by convection.

In a second exemplary embodiment, the present disclosure relates to a method for the collecting and fixating of microorganisms from a filtrate having a first density $D_1$, comprising the steps of providing a filter assembly, the filter assembly comprising an inlet and outlet and a reservoir to contain a second fluid having a second density $D_2$. A filter media is positioned within the filter assembly between the filter assembly inlet and outlet, wherein the filter media is positioned apart from the reservoir and within an interior space that is partitioned from the reservoir by a reservoir plate. The reservoir plate includes one opening for the flow of filtrate and at least two openings in communication with the reservoir and the interior space. This may then be followed by passing the filtrate through the filter assembly and collecting microorganisms and/or particulate material on the filter media and exposing the microorganisms and/or particulate material to the second fluid under the following conditions: (1) when the filtrate has a density $D_1$ that is greater than $D_2$, the filtrate flows out of the interior space into the reservoir and the second fluid replaces the filtrate in the interior space; or (2) when the filtrate has a density $D_1$ that is less than $D_2$ the second fluid flows from the reservoir into the interior space and the second fluid replaces the filtrate in the interior space. In the latter situation, the filter assembly may be inverted to promote the flow of the second fluid into the interior space to replace the filtrate.

BRIEF DESCRIPTION OF THE DRAWINGS

The features, operation and advantages of the invention may be better understood from the following detailed description of the preferred embodiments taken in conjunction with the attached drawings, in which.

DETAILED DESCRIPTION

Still other objects and advantages of the present invention will become readily apparent to those skilled in the art from the following detailed description, wherein it is shown and described preferred embodiments of the invention. As will be realized the invention is capable of other and different embodiments, and its several details are capable of modification in various respects, without departing from the invention. Accordingly, the description is to be regarded as illustrative in nature and not as restrictive.

Cutting edge microbial ecology is placing greater and greater emphasis on the collection of samples for subsequent metagenomic (DNA, ribosomal RNA [rRNA]; quantitative phylotyping of resident microbial biota), metatranscriptomic (messenger RNA [mRNA]; assessment of which metabolic genes are functioning) and metaproteomic (identity and magnitude of protein gene products produced) analyses for describing the identity and functioning of the microorganisms in their environment. One potential benefit of the approach herein is that this information may now be gathered without the need to cultivate the organisms in the laboratory, which at present captures less than 1% of the living microorganisms present in the environment. Collection of particulate material may therefore be essential and as the samples are now collected in situ over time, a method for the chemical preservation of this material that is now compatible with metagenomic, metatranscriptomic and metaproteomic analysis is also achieved.

The filter assembly of the present disclosure may therefore have a broad potential application of collection and preservation of filtered samples as collected by robotic time series water samplers for subsequent molecular analysis. The method and apparatus of the present disclosure is adaptable to any water sampling situation such as deep ocean sampling and may also be compatible with automated time series instrumentation. In addition, the sampling herein is applicable for collecting organisms and/or organic and/or inorganic particulate components such as suspended sediments, detritus, marine snow material, fecal material, etc. As bacteria will be a component of such collected material, it is important to preserve such collections in a manner where bacterial decomposition is prevented. If bacterial decomposition is not prevented, such would modify the composition and physical properties of the inanimate material under investigation.

Figure 1:
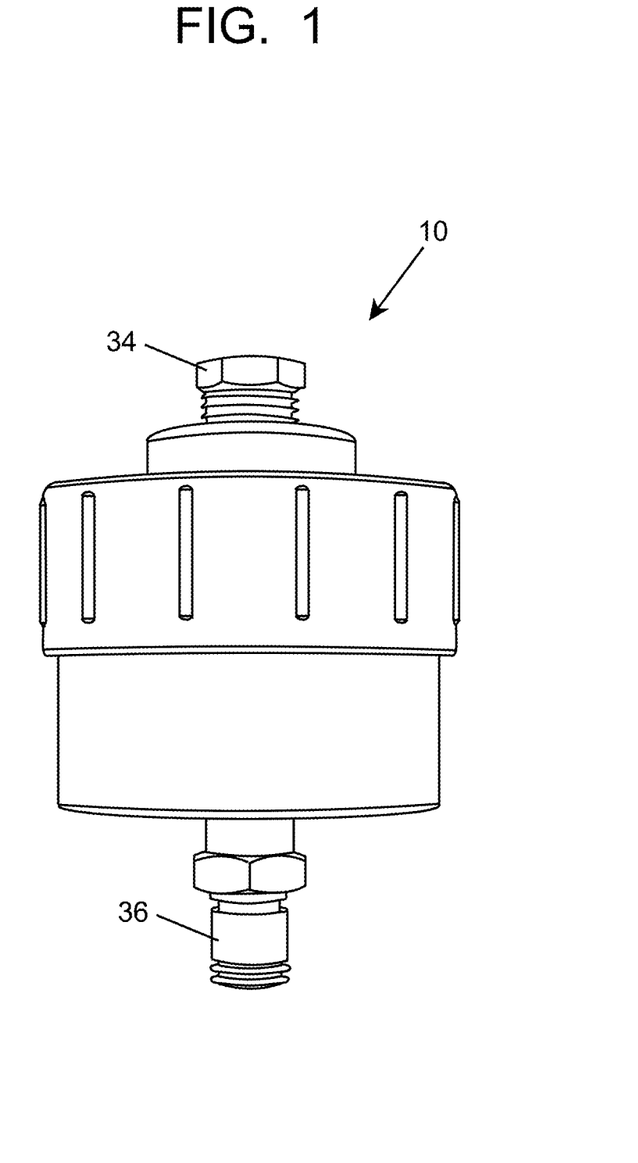
FIG. 1 is a front view of the filter assembly of the present disclosure.

The filter assembly of the present disclosure is shown in front view in FIG. 1. The assembly 10 is a stand-alone, in-line filter that, in addition to collecting particulate sample onto the surface of a filter media, is capable of chemically preserving the collected particulate sample via a physical process that requires no moving parts. Reference to "no moving parts" may be understood to mean that none of the components of the filter assembly need to move to provide filtration and preservation. Instead, the filter assembly utilizes laminar convective flow, driven by the differential in density between a chemical preservative (fixative) of the user's choosing that may be retained in the reservoir of the filter during sampling and the aqueous medium that the sample is being filtered from.

"Laminar convective flow" or "laminar convection" as used herein refers to the relatively smooth gravitational flow of fluids caused by a relative difference in the density of the fluids and may otherwise be known as gravitational convective flow. The force of gravity on two fluids of differing density in a common space may cause the higher density fluid to sink and displace the lower density fluid to an over-riding position relative to the higher density fluid.

"Preservative" or "fixative" as used herein refers to a material for preserving the structure of freshly collected biological specimen in a state most closely representing the structure and composition of the original living state. These materials may react chemically with tissue macromolecules, forming inter- and intra-molecular cross-links which increase the structural stability of the molecules. They may also inactivate autolytic enzymes and may make tissue more resistant to enzymatic degradation from autolysis and microbial activity These preservatives normally consist of at least two components, one or more active ingredients (fixatives) and a vehicle, often a buffering system. The vehicle may include materials such as metabolic poisons (azide, cyanide), divalent cations (Ca, Mg), penetrants (DMSO), surfactants (detergents—e.g. TWEEN), electrolytes or non-electrolytes added to adjust osmolarity.

The preservative may be, for instance, alcohol-based (methanol, ethanol, propanol, butanol), aldehyde-based (formaldehyde, glutaraldehyde), acid-based (acetic acid, dilute sulfuric acid), or mercury-based (mercuric chloride) depending on the subject being studied. Another preferred type, RNAlater® solution, available from Ambion, Austin, Tex., is an aqueous, nontoxic tissue storage reagent that rapidly permeates tissues to stabilize and protect cellular DNA and RNA. RNAlater® solution eliminates the need to immediately process tissue samples or to freeze samples in liquid nitrogen for later processing. Tissue pieces can be harvested and submerged in RNAlater® solution for storage without jeopardizing the quality or quantity of RNA/DNA obtained after subsequent RNA/DNA isolation.

The filter assembly 10 is a self-contained module with no moving parts that may further include an inlet 34 and an outlet 36 which may be fluidly connected to appropriate sample distribution valves and a source of flow (pump, suction, not shown). Active delivery of the preservative to the filtered sample occurs within the filter assembly 10, making the process quite simple in application and amendable to a variety of filtration applications.

Figure 2:
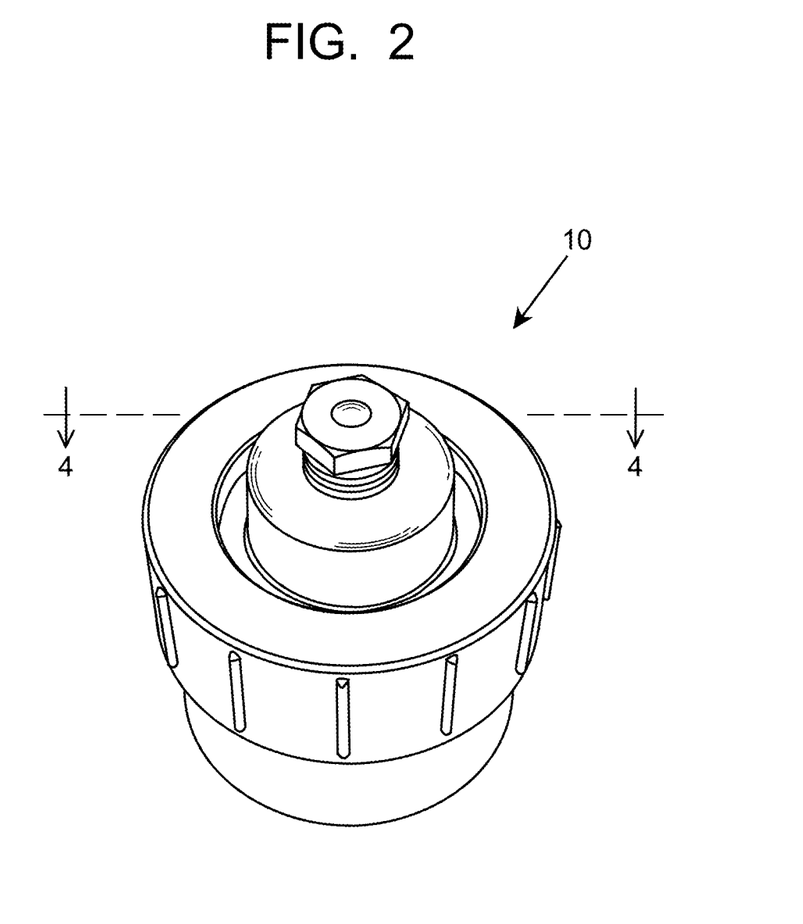
FIG. 2 is a perspective view of the filter assembly of FIG. 1.

FIG. 2 is a perspective view of the filter assembly of FIG. 1.

Figures 3, 3A:
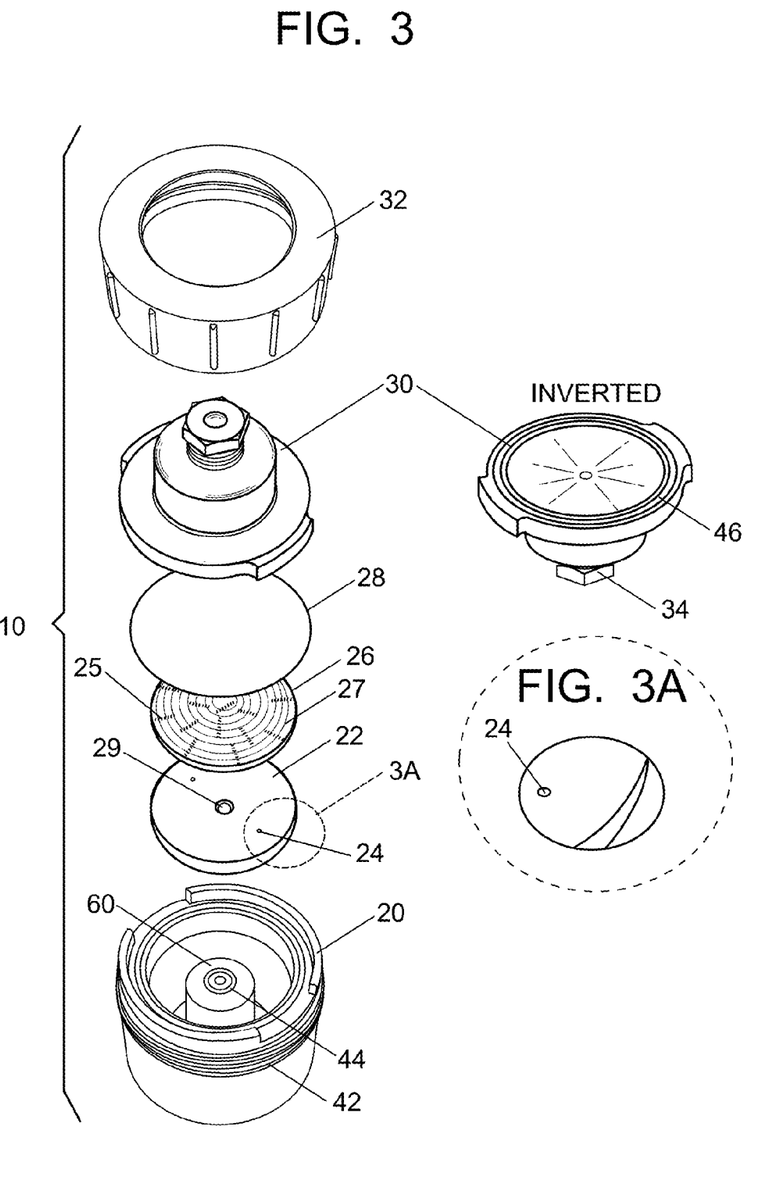
FIG. 3 is an exploded view of the filter assembly of FIG. 1.
FIG. 3A is an enlarged view of a portion of the reservoir plate of the filter assembly of FIG. 1.

FIG. 3 is an exploded view of the filter assembly of FIGS. 1 & 2 illustrating from bottom to top, an annular reservoir 20 that may contain the chemical preservative of the user's choosing, a sealed reservoir plate 22, a filter backup plate 26 that supports a filter media 28 and an overlying sample inlet plate 30 for closing out the assembly 10. Reference to a reservoir plate herein may be understood as any structure that serves to isolate the filter media from the reservoir and which also allows fluid flow through opening(s) therein to supply preservative to the filter media after filtration has taken place, as explained more fully herein.

The named components may be engaged together via a threaded cap 32 that may be screwed into outer threads located on the outside of the reservoir 20. A second o-ring 42 may be mounted on the reservoir to seal it to the cap 32. A third o-ring 44 may be located on the top of a center post 60 located in the center of the reservoir and may seal the reservoir 20 to the bottom of the reservoir plate 22. The reservoir plate 22 may further include an outlet 29 for the flow of filtrate out of the dead space 50. A fourth o-ring 46 may be mounted on the underside of the sample inlet plate 30 to further seal the assembly 10. It should be noted that other means of mechanical engagement of the components are also contemplated (such as clamping, bolting, etc.)

The named components, other than the filter media 28, may be molded of a relatively inert plastic (to the media that is being filtered, such as seawater, fresh water or brine solution) such as poly(vinyl chloride) (PVC). Other thermoplastics may include polyolefins, such as polyethylene, polypropylene, etc. The filter media may comprise any of a variety of filter materials including but not limited to, for instance, glass fibers, cellulose acetate fibers or a polycarbonate membrane that has been irradiated and etched to provide a plurality of relatively fine holes. One form of polycarbonate film that includes defined pore sizes are sold under the brand name Nuclepore™ and is available from Whatman, Ltd. The fibrous filters may be about 0.007-0.010 inches in thickness, while the polycarbonate membrane may be about 0.002-0.003 inches in thickness. Nominal pore size of the glass fiber filter may be about 0.8 µm, 0.22-0.45 µm for the cellulose acetate filter and about 0.1-0.45 µm for the polycarbonate membrane.

The filter assembly 10 may preferably be of a standard size for sampling, for instance 22 mm diameter, 47 or 50 mm diameter and 147 mm diameter. Accordingly, the filter diameter may be in the range of 15 mm to 200 mm.

Figure 4:
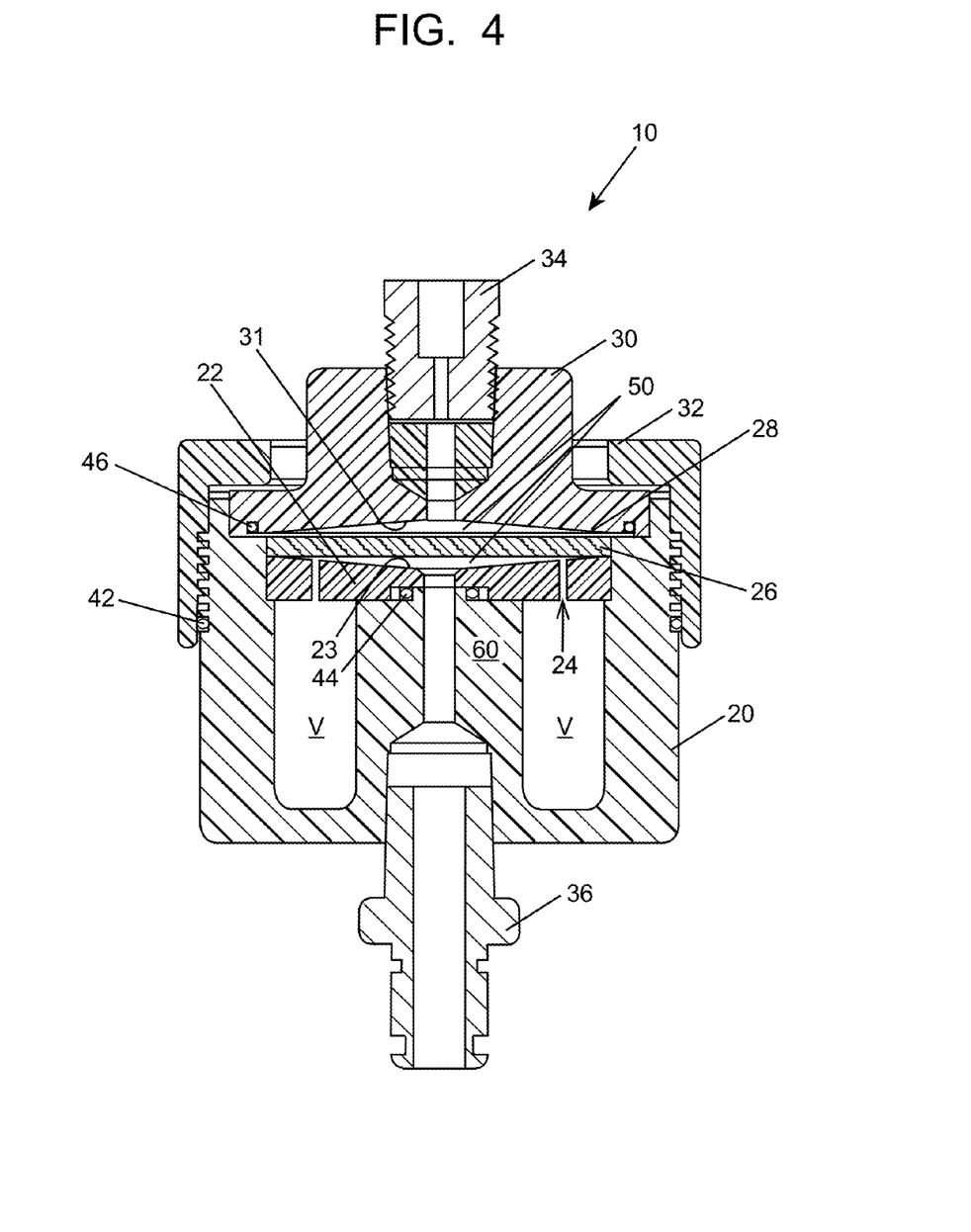
FIG. 4 is a cross-sectional view of the filter assembly of FIG. 2, taken along lines 4-4.

FIG. 4 is a cross-sectional view of the filter assembly of FIG. 2, taken along lines 4-4. Of particular note are the interior surfaces 31, 23 of the sample inlet plate 30 and reservoir plate 22, respectively, that each may preferably possess a conical taper to smoothly direct fluid flow through the filter assembly 10 and to capture the filter media 28 within a small back-to-back conical interior dead space 50. Such taper may be in the range of 1-15°, preferably 5-10° to minimize the volume of the dead space. Reference to a conical taper may be understood as that surface feature which changes from a relatively larger diameter to a relatively smaller diameter at a constant ratio. It may also be appreciated that the interior surfaces 31 and 23 may be concave, meaning that they may again change from a relatively larger diameter to a relatively smaller diameter, but not at a constant ratio. The use of a conical taper and/or a concave surface feature may provide relatively improved laminar flow of fluid such as the preservative fluid, described herein.

Again, fluid communication between the annular reservoir volume V and the conical interior dead space 50 of the filter assembly 10 may occur via the plurality of relatively small diameter holes 24 in the reservoir plate 22 which are in fluid communication with the filter backup plate. That is, fluid communication between the reservoir volume V and the conical interior 50 of the filter assembly 10 may initially occur via a plurality of relatively small diameter holes 24 (shown in enlarged perspective) in the reservoir plate 22.

The filter backup plate 26 may itself preferably include a plurality of concentric grooves 27 to aid in further distribution of the flow of the fluids within the filter unit. The filter backup plate 26 preferably includes radial scalloped grooves 25 that intersect the plurality of concentric grooves 27 to provide a fluid flow path between the backup plate 26 and the impinged filter media 28, Preferably, the holes 24 in the reservoir plate may vary in size relative to the volume of the filter unit and the fluids being filtered but may preferably be about 0.020±0.002 inches in diameter. Accordingly, the holes 24 may themselves preferably be in the range of about 0.015 inches to 0.025 inches in diameter. The filter unit includes an inlet 34 and outlet 36 which may have a hole size of preferably about 0.625 inches. It may be appreciated that the inlet and outlet are preferably of any dimension such that they are small enough such that one does not get an exchange of fluids into and out of the reservoir to occur within the same hole which will occur if the diameters are too large.

To better ensure that the flow paths of the preservative and the filtrate remain separated during operation, the two holes 24 may preferably be located radially at an angle of about 90-180° to each other. It is contemplated that more than 2 holes may be present. For example, one may utilize from 3-10 holes which may be located such that two separate flow paths are provided. In connection with the number of holes, a greater number of holes may increase the rate of preservative flow, it was also observed to increase the loss in preservative during filtration. Accordingly, a balance is struck between the flow rate and preservative loss, which was observed to be best achieved via the use of 2 holes, as noted above.

Figure 5A:
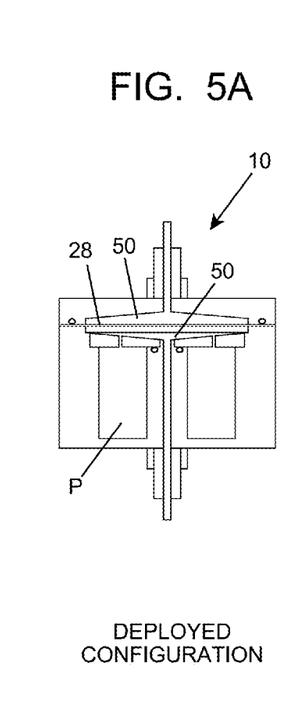
FIGS. 5A-5D are schematic views illustrating four phases in the filtering process of the filter assembly of the present disclosure.
Figure 5B:
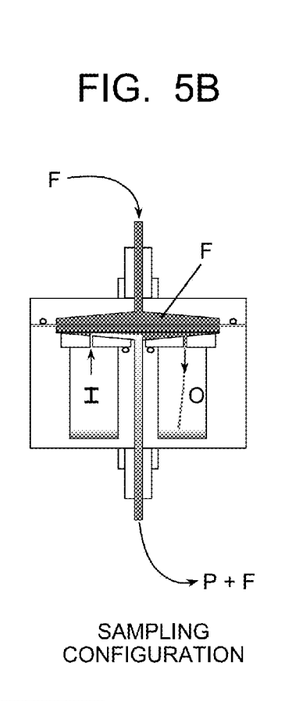

With attention directed to FIG. 5B, for laminar convective flow to occur in the filter unit 10, the two fluids, preservative P and filtrate F must differ in density. The difference in density between P and F may be plus or minus 0.01 g/cc, which may then be sufficient to sustain laminar convective flow. Greater difference in densities between the fluids may provide relatively faster flow. For example, the difference in density may be plus or minus 0.05 g/cc, or plus or minus 0.01 g/cc up to 0.50 g/cc. Accordingly, the difference in density between the preservative P and the filtrate F may be in the range of plus or minus 0.01 g/cc up to 0.50 g/cc. Convective flow is then initiated when one of the holes is exposed to filtrate with the indicated density differences. Convective flow is particularly preferred in such filtering applications as disclosed herein because diffusion of the preservative through the filter media is a relatively slow process while convective flow is relatively faster.

FIGS. 5A-5D schematically illustrates the functioning of the filter assembly 10 using a gray die F to represent the path of flow of the filtrate. The filter assembly 10 in its deployed configuration, ready for use, for instance in a body of sea water, is shown in FIG. 5A. The interior volume V of the filter assembly 10 is hermetically filled with the preservative P (shown as clear in FIGS. 5A-5D). Upon the initiation of filtration or sample procurement as shown in FIG. 5B, the conical dead space 50 within the filter assembly 10 is flushed free of the preservative P due to the flow of the heavier (higher density) filtrate F (sea water shown as gray in FIGS. 5A-5D) that flows into the filter assembly 10 and displaces the lighter (less dense) preservative in the conical dead space 50. The preservative P is swept from above the filter media 28 such that the sample to be collected is not exposed to the preservative during filtration (FIG. 5B).

Because the reservoir remains filled at all times, any preservative "I" that convects through one or more of the holes 24 must be balanced with an equal volume of the filtered medium "O" entering the other hole 24 which holes 24 may be radially displaced form one another. The density differential between the preservative P and the sample filtrate F, for instance sea water, causes laminar convective flow to be initiated and the lower density preservative fluid P to flow to a relative position above the higher density fluid F. The rate of flow may be controlled by the size of the two holes 24. During filtration, the filter media 28 is not exposed to preservative P because filtrate is being continuously passed through the media 28 to outlet 36. It is also worth noting that during filtration, FIG. 5B, the preservative exiting the reservoir from the conical dead space is immediately flushed from the assembly along with filtrate that has been filtered.

Figure 5C:
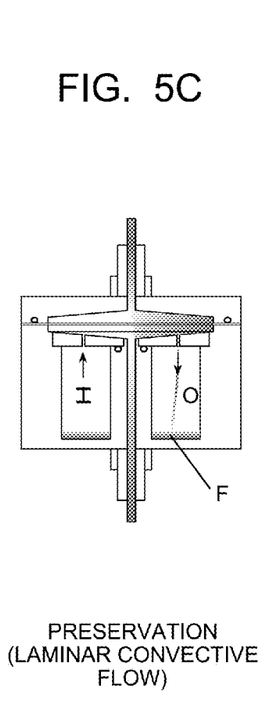
Figure 5D:
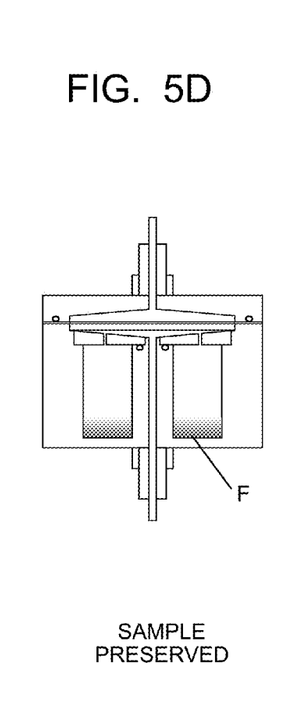

When filtration is stopped, the preservative P undergoes laminar convective flow proceeding under the filter backup plate 26 in the conical dead space 50 (see FIG. 4) and also penetrates the filter media 28. This then serves to chemically preserve the particulate matter accumulated on the surface of the filter (FIG. 5C). This preservation may preferably take place over a period of less than or equal to 30 minutes depending upon the difference in density between the preservative and filtrate. The rate of preservative delivery may be linearly dependent on the density difference between the preservative and the filtrate. For example, when the difference in density is about 0.03 g/cc, the preservation cycle may occur over a period of 15-20 minutes without the need for any mechanical manipulation. Eventually, the filter assembly 10 again achieves equilibrium with respect to the different density fluids, maintaining the preservation of the sample (FIG. 5D). It may be appreciated that the relatively lower density preservative ultimately covers the filter media thereby replacing the relatively dense seawater which seawater may flow to the bottom of the reservoir 20.

The example illustrated in FIGS. 5A-5D applies when the preservative/fixative P is of a lower density than the medium F being filtered. When the preservative P has a greater density than the medium F being filtered, the filter assembly 10 may be inverted to function as described. In that instance, the preservative P may flow in a downward direction during laminar convective flow, as opposed to an upward direction when the preservative is of lower density. The filter may then again be isolated and the sample collected and examined. The sample may comprise, for instance biological and inanimate particulate specimen.

Figure 6:
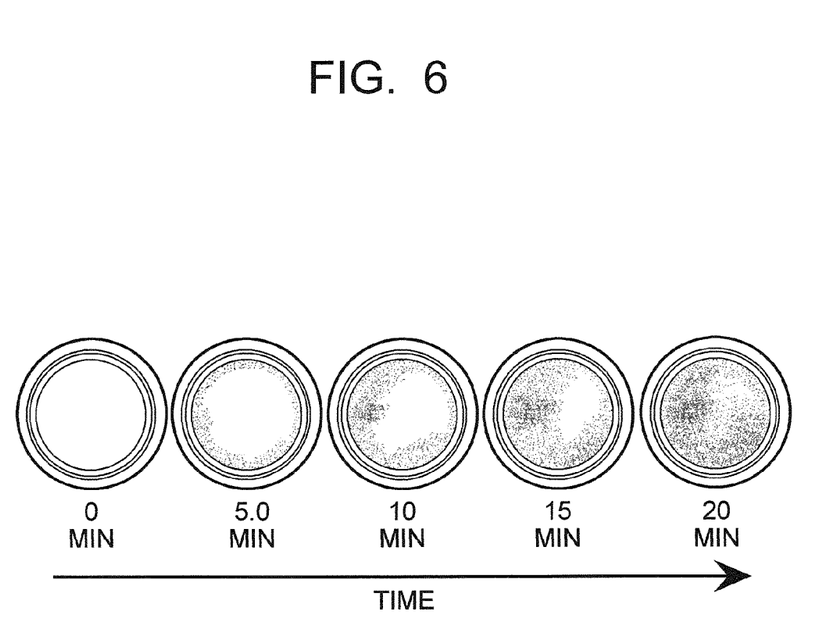
FIG. 6 is a time lapse illustration of the laminar convection process, looking down on the filter media, where a dye is used in place of a preservative (see below) and has a density that is less than the medium being filtered.

FIG. 6 is a time lapse illustration of the laminar convective flow process, looking down on the filter media, where a dye is used in place of the preservative and has a density that is less than the medium being filtered. As can be seen, the filter at the beginning of the laminar convection process (time zero or OT) is clear, as no dye has flowed into or through the filter. As the time duration progresses (5, 10, 15, 20 minutes), the filter is shown to change color (increasingly more gray) as the dye flows through and colors the filter. Accordingly, time lapse photography confirms that the dye penetrates the filter media by laminar convection. Depending upon the magnitude of the difference in density between the fluids, the duration may be less than or greater than 20 minutes.

More specifically, in the example in FIG. 6 the density contrast between the filtrate (D~1.03 g/cc) and the preservative density (~1.00 g/cc) is about 3.0%. If the density contrast between the filtrate and preservative is greater (for example RNAlater® has a density of ~1.22 g/cc, seawater is ~1.03 g/cc, density contrast 19.0%) the rate of delivery of the preservative will be several times faster, which is beneficial, preserving the sample in about 7-8 minutes. On the other hand, the loss of preservative during filtration will be similarly greater, which is not advantageous.

The filter assemblies of the present disclosure may have a broad potential application, that of collection and preservation of filtered samples as collected by robotic time series water samplers for subsequent molecular analysis. The filter assembly of the present disclosure is operationally effective in deep water environments where one may desire to minimize moving parts and maximize compatibility with automated time series instrumentation. Because the assembly is a self-contained module with no moving parts there is now no need for any other connections other than an inlet and outlet for the filtrate (e.g. seawater). There also may be no need for connection to an electromechanical device for active delivery of the preservative to the filtered sample. This provides for the feature that the filter assembly herein is amendable to a variety of filtration applications where minimization of mechanical steps is desirable or essential.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for the collecting and fixating of microorganisms from a filtrate having a first density $D_1$, comprising the steps of:

providing a filter assembly, the filter assembly comprising an inlet and outlet and a reservoir to contain a second fluid having a second density $D_2$; a filter media within the filter assembly between said filter assembly inlet and outlet and wherein said filter media is positioned apart from the reservoir and within an interior space that is partitioned from the reservoir by a reservoir plate; said reservoir plate including one opening for said flow of filtrate and at least two openings in communication with said reservoir and said interior space;

passing said filtrate through said filter assembly and collecting microorganisms and/or particulate material on said filter media;

exposing said microorganisms and/or particular material to said second fluid under the following conditions:

(1) when said filtrate has a density $D_1$ that is greater than $D_2$, said filtrate flows out of said interior space into said reservoir and said second fluid replaces said filtrate in said interior space; or (2) when said filtrate has a density $D_1$ that is less than $D_2$ said second fluid flows from said reservoir into said interior space and said second fluid replaces said filtrate in said interior space.

2. The method of claim 1 further including an inlet plate having a surface, and wherein said reservoir plate has a surface, and wherein said surface of said inlet plate and said surface of said reservoir plate form said interior space.

3. The method of claim 2 wherein said surface of said reservoir plate and said surface of said inlet plate have a conical taper.

4. The method of claim 2 wherein said surface of said reservoir plate and said surface of said inlet plate are concave.

5. The method of claim 1 wherein said filter media is at least partially supported in said space by a filter backup plate.

6. The method of claim 1 wherein said filtrate that flows out of said interior space into said reservoir undergoes laminar convective flow.

7. The method of claim 1 wherein said second fluid that flows from said reservoir into said interior space undergoes laminar flow.

8. The method of claim 1 wherein said second fluid is a preservative for a biological specimen or inanimate particulate specimen.

9. The method of claim 1 wherein said first fluid is seawater, fresh water or brine solution.

10. The method of claim 1 wherein $D_1$ and $D_2$ differ in density by ±0.01 g/cc to 0.50 g/cc.

11. The method of claim 8 wherein said preservative operates to reduce RNA degradation of a specimen contained in said filtrate.

12. The method of claim 1 wherein said filter media is one of glass fibers, cellulose acetate fibers or a polycarbonate membrane.

* * * * *